US010667876B2

(12) United States Patent
Maillet et al.

(10) Patent No.: US 10,667,876 B2
(45) Date of Patent: Jun. 2, 2020

(54) ROBOTIC-ASSISTED DEVICE FOR POSITIONING A SURGICAL INSTRUMENT RELATIVE TO THE BODY OF A PATIENT

(71) Applicant: MedTech S.A., Montpellier (FR)

(72) Inventors: Pierre Maillet, Saint Aunes (FR);
Bertin Nahum, Baillargues (FR);
Fernand Badano, Villeurbanne (FR);
Patrick Dehour, Crespian (FR)

(73) Assignee: MedTech S.A., Montpellier (FR)

(*) Notice: Subject to any disclaimer, the term of this patent is extended or adjusted under 35 U.S.C. 154(b) by 0 days.

(21) Appl. No.: 16/225,693

(22) Filed: Dec. 19, 2018

(65) Prior Publication Data
US 2019/0125460 A1    May 2, 2019

Related U.S. Application Data

(63) Continuation of application No. 15/419,675, filed on Jan. 30, 2017, now Pat. No. 10,159,534, which is a
(Continued)

(30) Foreign Application Priority Data

Nov. 30, 2011    (FR) .................................... 11 60974

(51) Int. Cl.
*A61B 34/20* (2016.01)
*A61B 34/32* (2016.01)
(Continued)

(52) U.S. Cl.
CPC .............. *A61B 34/32* (2016.02); *A61B 17/32* (2013.01); *A61B 34/20* (2016.02); *A61B 34/30* (2016.02);
(Continued)

(58) Field of Classification Search
CPC ......... A61B 34/32; A61B 34/20; A61B 34/30; A61B 90/39; A61B 17/32; B25J 9/0087; B25J 19/026
(Continued)

(56) References Cited

U.S. PATENT DOCUMENTS

| 4,549,540 A | 10/1985 | Caspari et al. |
| 4,722,056 A | 1/1988 | Roberts et al. |

(Continued)

FOREIGN PATENT DOCUMENTS

| CN | ZL201280059414.5 | 9/2017 |
| CN | 107550566 A | 1/2018 |

(Continued)

OTHER PUBLICATIONS

"U.S. Appl. No. 14/361,273, Final Office Action dated May 5, 2016", 12 pgs.
(Continued)

*Primary Examiner* — Thomas G Black
*Assistant Examiner* — Wae L Louie
(74) *Attorney, Agent, or Firm* — Schwegman Lundberg & Woessner, P.A.

(57) ABSTRACT

The robotic device for positioning a surgical instrument relative to the body of a patient includes a first robotic arm with a device for rigidly connecting to at least one surgical instrument, a device for anatomical realignment of the first arm by realigning an image that is of an area of the anatomy of the patient, and a device for compensating the movements of the first arm on the basis of detected movements. One version of the device includes at least one second robotic arm having sensors for detecting inner movements of the anatomical area, and a device for controlling the positioning of the first arm relative to sensed inner movements and to the outer movements induced in the second arm.

20 Claims, 1 Drawing Sheet

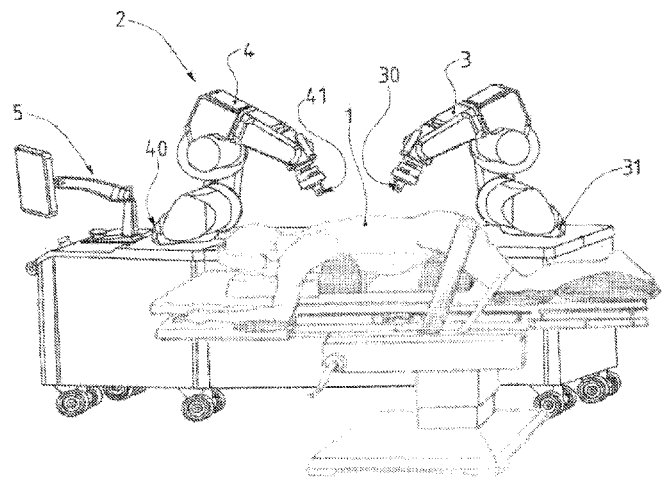

Related U.S. Application Data continuation of application No. 14/361,273, filed as application No. PCT/FR2012/052582 on Nov. 8, 2012, now Pat. No. 9,592,096.

(51) Int. Cl.
| | |
|---|---|
| *A61B 34/30* | (2016.01) |
| *A61B 34/00* | (2016.01) |
| *A61B 90/00* | (2016.01) |
| *A61B 17/32* | (2006.01) |
| *B25J 9/00* | (2006.01) |
| *B25J 19/02* | (2006.01) |
| *A61B 17/00* | (2006.01) |

(52) U.S. Cl.
CPC .............. *A61B 34/76* (2016.02); *A61B 90/39* (2016.02); *B25J 9/0087* (2013.01); *B25J 19/026* (2013.01); *A61B 2017/00694* (2013.01); *A61B 2017/00699* (2013.01); *A61B 2034/2046* (2016.02); *A61B 2034/2063* (2016.02); *A61B 2034/2065* (2016.02); *A61B 2034/2072* (2016.02); *A61B 2090/364* (2016.02); *A61B 2090/376* (2016.02); *A61B 2090/378* (2016.02); *Y10S 901/08* (2013.01)

(58) Field of Classification Search
USPC .................................................. 700/251, 245
See application file for complete search history.

(56) References Cited

U.S. PATENT DOCUMENTS

| | | | |
|---|---|---|---|
| 4,913,413 A | 4/1990 | Raab et al. | |
| 5,383,454 A | 1/1995 | Bucholz | |
| 5,389,101 A | 2/1995 | Heilbrun et al. | |
| 5,403,319 A | 4/1995 | Matsen, III et al. | |
| 5,603,318 A | 2/1997 | Heilbrun et al. | |
| 5,799,055 A | 8/1998 | Peshkin et al. | |
| 5,871,018 A | 2/1999 | Delp et al. | |
| 5,976,122 A | 11/1999 | Madhani et al. | |
| 6,033,415 A | 3/2000 | Mittelstadt et al. | |
| 6,167,292 A * | 12/2000 | Badano ................... | A61B 90/39 600/407 |
| 6,226,548 B1 | 5/2001 | Foley et al. | |
| 6,298,262 B1 | 10/2001 | Franck et al. | |
| 6,322,567 B1 | 11/2001 | Mittelstadt et al. | |
| 6,459,926 B1 | 10/2002 | Nowlin et al. | |
| 6,493,608 B1 | 12/2002 | Niemeyer | |
| 6,584,174 B2 | 6/2003 | Schubert et al. | |
| 6,609,022 B2 | 8/2003 | Vilsmeier et al. | |
| 6,772,002 B2 | 8/2004 | Schmidt et al. | |
| 6,873,867 B2 | 3/2005 | Vilsmeier | |
| 7,203,277 B2 | 4/2007 | Birkenbach et al. | |
| 7,213,975 B2 * | 5/2007 | Khemakhem ........ | G02B 6/3817 385/101 |
| 7,227,981 B1 | 6/2007 | Fleute et al. | |
| 7,366,562 B2 | 4/2008 | Dukesherer et al. | |
| 7,463,823 B2 | 12/2008 | Birkenbach et al. | |
| 7,542,791 B2 | 6/2009 | Mire et al. | |
| 7,561,733 B2 | 7/2009 | Vilsmeier et al. | |
| 7,567,834 B2 | 7/2009 | Clayton et al. | |
| 7,599,730 B2 | 10/2009 | Hunter et al. | |
| 7,623,702 B2 | 11/2009 | Arata et al. | |
| 7,697,972 B2 | 4/2010 | Verard et al. | |
| 7,713,205 B2 * | 5/2010 | Fu ............................ | A61B 8/08 600/437 |
| 7,747,311 B2 | 6/2010 | Quaid, III | |
| 7,751,865 B2 | 7/2010 | Jascob et al. | |
| 7,763,035 B2 | 7/2010 | Melkent et al. | |
| 7,771,436 B2 | 8/2010 | Moctezuma De La Barrera et al. | |
| 7,831,292 B2 | 11/2010 | Quaid et al. | |
| 7,840,253 B2 | 11/2010 | Tremblay et al. | |
| 7,843,158 B2 | 11/2010 | Prisco | |
| 7,873,400 B2 | 1/2011 | Moctezuma De La Barrera et al. | |
| 8,064,985 B2 | 11/2011 | Peterson | |
| 8,095,200 B2 | 1/2012 | Quaid, III | |
| 8,239,001 B2 | 8/2012 | Verard et al. | |
| 8,287,522 B2 | 10/2012 | Moses et al. | |
| 8,311,611 B2 | 11/2012 | Csavoy et al. | |
| 8,339,447 B2 | 12/2012 | Riederer | |
| 8,394,144 B2 | 3/2013 | Zehavi et al. | |
| 8,412,308 B2 | 4/2013 | Goldbach | |
| 8,498,744 B2 | 7/2013 | Odermatt et al. | |
| 8,509,503 B2 | 8/2013 | Nahum et al. | |
| 8,644,907 B2 | 2/2014 | Hartmann et al. | |
| 8,657,809 B2 | 2/2014 | Schoepp | |
| 8,753,346 B2 | 6/2014 | Suarez et al. | |
| 8,918,212 B2 | 12/2014 | Larkin et al. | |
| 8,977,021 B2 | 3/2015 | Kang et al. | |
| 8,992,542 B2 | 3/2015 | Hagag et al. | |
| 8,992,580 B2 | 3/2015 | Bar et al. | |
| 8,996,169 B2 | 3/2015 | Lightcap et al. | |
| 9,082,319 B2 | 7/2015 | Shimada et al. | |
| 9,125,680 B2 | 9/2015 | Kostrzewski et al. | |
| 9,138,129 B2 * | 9/2015 | Diolaiti ............... | A61B 1/00163 |
| 9,237,861 B2 | 1/2016 | Nahum et al. | |
| 9,469,034 B2 * | 10/2016 | Diolaiti ............... | A61B 1/00087 |
| 9,592,096 B2 * | 3/2017 | Maillet .................. | B25J 19/026 |
| 10,159,534 B2 * | 12/2018 | Maillet .................. | A61B 90/39 |
| 10,220,843 B2 * | 3/2019 | Coulter .................. | B60L 50/50 |
| 2002/0177843 A1 * | 11/2002 | Anderson ............. | A61B 34/70 606/1 |
| 2003/0130665 A1 | 7/2003 | Pinczewski et al. | |
| 2004/0024311 A1 | 2/2004 | Quaid, III | |
| 2004/0111183 A1 | 6/2004 | Sutherland et al. | |
| 2004/0243109 A1 | 12/2004 | Tovey et al. | |
| 2006/0100642 A1 | 5/2006 | Yang et al. | |
| 2006/0142657 A1 * | 6/2006 | Quaid ................. | A61B 17/1675 600/424 |
| 2007/0002926 A1 | 1/2007 | Mcdonald et al. | |
| 2007/0013336 A1 * | 1/2007 | Nowlin .................. | A61B 34/71 318/568.21 |
| 2007/0106306 A1 | 5/2007 | Bodduluri et al. | |
| 2007/0142970 A1 * | 6/2007 | Burbank ................. | C10J 3/721 700/251 |
| 2007/0156017 A1 * | 7/2007 | Lamprecht ......... | A61B 1/00193 600/102 |
| 2007/0156157 A1 | 7/2007 | Nahum et al. | |
| 2007/0185485 A1 | 8/2007 | Hauck et al. | |
| 2007/0270687 A1 | 11/2007 | Gardi et al. | |
| 2007/0270690 A1 | 11/2007 | Woerlein | |
| 2008/0033410 A1 * | 2/2008 | Rastegar ................ | A61B 18/20 606/9 |
| 2008/0037714 A1 | 2/2008 | Sakaida et al. | |
| 2008/0208212 A1 | 8/2008 | Camus et al. | |
| 2009/0036918 A1 | 2/2009 | Burgess | |
| 2009/0088634 A1 * | 4/2009 | Zhao ...................... | B25J 9/1689 600/427 |
| 2009/0177081 A1 | 7/2009 | Joskowicz et al. | |
| 2009/0245600 A1 * | 10/2009 | Hoffman ............... | H04N 13/366 382/128 |
| 2010/0056905 A1 * | 3/2010 | Anderson ............. | G01S 5/0215 600/424 |
| 2010/0063514 A1 | 3/2010 | Maschke | |
| 2011/0277775 A1 * | 11/2011 | Holop ...................... | B32B 3/12 128/849 |
| 2012/0310255 A1 * | 12/2012 | Brisson ................ | A61B 17/295 606/130 |
| 2013/0105552 A1 * | 5/2013 | Weir ................ | A61B 17/07207 227/180.1 |
| 2014/0350571 A1 * | 11/2014 | Maillet .................. | B25J 19/026 606/130 |
| 2014/0371577 A1 | 12/2014 | Maillet et al. | |
| 2015/0151783 A1 * | 6/2015 | Kitazume ............ | B62D 5/0472 701/42 |
| 2015/0178468 A1 | 6/2015 | Kang et al. | |
| 2017/0202629 A1 | 7/2017 | Maillet et al. | |

(56) References Cited

U.S. PATENT DOCUMENTS

| | | | |
|---|---|---|---|
| 2018/0049798 A1* | 2/2018 | Shelton, IV | A61B 34/30 |
| 2019/0125460 A1* | 5/2019 | Maillet | A61B 90/39 |

FOREIGN PATENT DOCUMENTS

| | | |
|---|---|---|
| DE | 102008022924 | 11/2009 |
| EP | 1680007 B1 | 4/2013 |
| EP | 1993482 B1 | 9/2014 |
| JP | 11309 A | 1/1999 |
| JP | 2001252268 A | 9/2001 |
| JP | 2008161266 A | 7/2008 |
| JP | 2009537915 A | 10/2009 |
| WO | WO-9414366 A2 | 7/1994 |
| WO | WO-9838908 A1 | 9/1998 |
| WO | WO-0207612 A1 | 1/2002 |
| WO | WO-02061709 | 8/2002 |
| WO | WO-03043515 A1 | 5/2003 |
| WO | WO-2005032390 A1 | 4/2005 |
| WO | WO-2005122916 A1 | 12/2005 |
| WO | WO-2007002926 A2 | 1/2007 |
| WO | WO-2007113713 A2 | 10/2007 |
| WO | WO-2011063715 A1 | 6/2011 |

OTHER PUBLICATIONS

"U.S. Appl. No. 14/361,273, Non Final Office Action dated Sep. 15, 2015", 13 pgs.
"U.S. Appl. No. 14/361,273, Notice of Allowance dated Nov. 4, 2016", 10 pgs.
"U.S. Appl. No. 14/361,273, Preliminary Amendment filed May 28, 2014", 9 pgs.
"U.S. Appl. No. 14/361,273, Response filed Jan. 15, 2016 to Non Final Office Action datd Sep. 15, 2015", 13 pgs.
"U.S. Appl. No. 14/361,273, Response filed Oct. 19, 2016 to Final Office Action dated May 5, 2016", 6 pgs.
"U.S. Appl. No. 15/419,675, Non Final Office Action dated Mar. 27, 2018", 11 pgs.
"U.S. Appl. No. 15/419,675, Notice of Allowance dated Jul. 31, 2018", 10 pgs.
"U.S. Appl. No. 15/419,675, Preliminary Amendment filed Apr. 7, 2017", 6 pgs.
"U.S. Appl. No. 15/419,675, Response filed Jun. 27, 2018 to Non Final Office action dated Mar. 27, 2018", 10 pgs.
"Chinese Application Serial No. 201280059415.5, Office Action dated Mar. 16, 2017", (W/ English Translation), 7 pgs.
"Chinese Application Serial No. 201280059415.5, Response filed Jan. 9, 2017 to Office Action dated Aug. 23, 2016", (W/ English Translation), 11 pgs.
"European Application Serial No. 12795507.8, Response filed Aug. 19, 2014 to Communication pursuant to Rules 161(2) and 162 EPC dated Jul. 8, 2014", 9 pgs.
"European Application Serial No. 18171878.4, Office Action dated Aug. 29, 2018", not in English, 8 pgs.
"International Application Serial No. PCT/FR2012/052582, International Preliminary Report on Patentability dated Jun. 12, 2014", 8 pgs.
"International Application Serial No. PCT/FR2012/052582, International Search Report dated Apr. 15, 2013", 3 pgs.
"International Application Serial No. PCT/FR2012/052582, Written Opinion dated Apr. 15, 2013", 8 pgs.
Comparetti, et al., "Accurate multi-robot targeting for keyhole neurosurgery based on external sensor monitoring", Proc Inst Mech Eng H; 226(5);, (May 2012), 347-59.
Cruces, et al., "Cooperative Robotic System to Support Surgical Interventions (Chap. 35)", In Medical Robotics; Bozovic (Ed.); I-Tech Education and Publishing;, (Jan. 2008), 481-490.

Danilchenko, et al., "Robotic Mastoidectomy", Otol Neurotol; 32(1), (Jan. 2011), 11-16.
Haidegger, et al., "Accuracy Improvement of a Neurosurgical Robot System", Proc. of the 2nd IEEERAS/EMBS Int'l Conf Biomedical Robotics and Biomechatronics (BioRob); Scottsdale, AZ, (Oct. 19-22, 2008), 836-841.
Haidegger, T, "Improving the Accuracy and Safety of a Robotic System for Neurosurgery (thesis)", Johns Hopkins University; Center for Computer-Integrated Surgical Systems and Technology, (May 27, 2008), 93 pgs.
Heinig, "Design and Evaluation of the Motor Assisted Robotic Stereotaxy System MARS", (Dissertation); Universitat zu Lubeck, Institut fur Robotik und Kognitive Systeme;, (Sep. 2012), 190 pgs.
Howe, Robert D, et al., "Robotics for Surgery", Annual Rev. Biomed. Eng., (1999), 211-240.
Kienzle, et al., "Total Knee Replacement", IEEE Engineering in Medicine and Biology Magazine, vol. 14, No. 3, (May 1, 1995), 301-306.
Li, et al., "The application accuracy of the NeuroMate robot—A quantitative comparison with frameless and frame-based surgical localization systems", Comput Aided Surg.; 7(2);, (Jun. 21, 2002), 90-98.
Lin, et al., "A miniature patient-mount navigation system for assisting needle placement in CT-guided intervention", International Journal on Medical Robotics and Computer Assisted Surgery 7(4 );, (Dec. 2011), 423-430.
Nahum, et al., "Method for the Automated and Assisted Acquisition of Anatomical Surfaces", U.S. Appl. No. 14/949,822, filed Nov. 23, 2015.
Ortmaier, T., et al., "A Hands-On-Robot for Accurate Placement of Pedicle Screws", Proceedings of the 2006 IEEE International Conference on Robotics and Automation, (May 2006), p. 4179-4186.
Richter, et al., "Robust real-time robotRworld calibration for robotized transcranial magnetic stimulation", International Journal on Medical Robotics and Computer Assisted Surgery; 7(4 );, (Dec. 2011), 414-422.
Ruby, S, "Miniature robot system for keyhole neurosurgery, A thesis submtted in fulfillment of the requirements for the degree of Master of Science", The Selim and Rachel Benin School of Engineering and Computer Science; The Hebrew Univ. of Jerusalem; Jerusalem, Israel;, (Nov. 13, 2005), 63 pgs.
Tovar-Arriaga, et al., "Development of a robotic FD-CT-guided navigation system for needle placement R preliminary accuracy tests", International Journal on Medical Robotics and Computer Assisted Surgery; 7(2), (Jun. 2011), 225-236.
Troccaz, "Capteurs et recalage per-operatoires en robotique medicale (in French w/Machine Transl. of Intro. and Conclusion)", HAL Id: cel-00344721, version 1;, [Online] Retrieved from the internet: <http://cel.archives-ouvertes.fr/docs/00/34/47/21/PDF/Recalage-per-op-robots-medicaux.pdf>, (Dec. 1, 2008), 1-32.
Xia, et al., "An integrated system for planning, navigation and robotic assistance for skull base surgery", In J Med Rob.; (Author Manuscript; 20 pgs.); 4(4);, (Dec. 2008), 321-330.
U.S. Appl. No. 14/361,273 U.S. Pat. No. 9,592,096, filed May 28, 2014, Robotic-Assisted Device for Positioning a Surgical Instrument Relative to the Body of a Patient.
U.S. Appl. No. 15/419,675, filed Jan. 30, 2017, Robotic-Assisted Device for Positioning a Surgical Instrument Relative to the Body of a Patient.
"Chinese Application Serial No. 201280059145.5, Response filed May 31, 2017 to Office Action dated Mar. 16, 2017", 2 pgs.
"Chinese Application Serial No. 201710777402.6, Office Action dated Oct. 25, 2019", w/ English Translation, 12 pgs.
"European Application Serial No. 18171878.4, Response filed Mar. 26, 2019 to Office Action dated Aug. 29, 2018", 34 pgs.

* cited by examiner

ROBOTIC-ASSISTED DEVICE FOR POSITIONING A SURGICAL INSTRUMENT RELATIVE TO THE BODY OF A PATIENT

CROSS REFERENCE TO RELATED APPLICATIONS

This application is a continuation of U.S. application Ser. No. 14/361,273, filed May 28, 2014, which is the national stage of International Application No. PCT/FR2012/052582, filed Nov. 8, 2012, which claims priority to FR 11 60974, filed Nov. 30, 2011, each of which is herein incorporated by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention falls within the medical field, especially in the operating methodology when preparing and conducting surgical operations.

The invention specifically relates to anatomical medical imaging, in order to perform robotic-assisted surgical operations.

The present invention will find a preferred, but in no way restricted, application to surgical operations of the anatomical region of the rachis.

To this end, the invention relates to a device for positioning a surgical instrument relative to the body of a patient.

It should be noted that the invention will be described according to a specific example of operation at the level of the lumbar rachis, the level of the anterior curvature of the lordosis of the spine. However, the invention can be used for an operation at the level of the upper and lower cervical rachis, the back or thoracic rachis, as well as the sacral rachis and the coccyx.

2. Description of Related Art Including Information Disclosed Under 37 CFR 1.97 and 37 CFR 1.98

In this anatomical area, surgical procedures are delicate, thorough and risky operations that require accurately drilling, breaking or milling a vertebra, dissecting muscles, ligaments, vertebral discs, while avoiding damaging the spinal cord, the nerve roots, the veins and the nerves.

For example, the commonly performed procedures include laminectomy, radicular release, in the cases of lumbar spinal stenosis or a herniated disc; arthrodesis consisting in combining vertebrae by screwing into a pedicle, kyphoplasty and vertebroplasty consisting in injecting a cement into the vertebral body.

Such operations are implemented through an as narrow as possible operating channel, in order to reduce hospitalization and facilitate the patient's recovery, even more through a minimally invasive or percutaneous surgery. The narrowness of this operating channel makes the precision of the operation by the practitioner difficult, since the visibility decreases due to bleeding. In this condition, a rate of misplacement of pedicle screws up to 25% results, knowing that the aggressive misplacements make up 3 to 5%.

In order to improve the accuracy of his operation, the surgeon now uses anatomical medical imaging systems, in particular fluoroscopy and navigation.

First of all, fluoroscopy generates X-rays over a period permitting to acquire images continuously and thus achieve a direct view, where the surgeon can monitor in real time the progress of his tool within the anatomical structure. However, since extended or repeated exposure to these ionizing radiations is harmful to the medical personnel and the patient, the use of this technique is deliberately limited.

On the other hand, navigation permits to view a virtual tool on a pre- or per-operative imaging, on which the surgeon observes in real time the progress of his tool, even more so in the case of a three-dimensional (3D) navigation.

However, a first drawback arises from the complexity of the calculations of for positioning the surgical tools, leading to approximations and causing wrong positioning. In addition, the existing techniques require positioning a fixed marker on the patient's body, presently invasively screwed into the spine, for example, and to which the image-acquisition optics of the navigation system is pointed.

Furthermore, these techniques do not permit to cope with the errors related to the manual performance of the surgical procedure by the practitioner, in particular in the case of a stressing step of drilling, then screwing into a pedicle.

That is why robotic systems for assisting surgery have been developed, which permit to assist the surgeon and to mechanically ensure accuracy and repeatability of the surgical procedure.

In this context, an additional problem during an operation lies in the management of the anatomical movements of the patient due to his own breathing as well as to his heart beating. In particular, the breathing depends on the activity of the diaphragm generating chest and lung movements contributing to the gas exchanges. This muscular activity causes a deformation of the collateral anatomical parts, such as the abdomen and the rachis. The magnitude of this deformation depends on the minute ventilation (MV), depending on its volume and its frequency, but also on the position of the patient, namely standing, sitting or lying on his stomach, back or side.

In the case of an operation on the rachis, the latter moves to a larger extent for the thoracic vertebrae and to a lesser extent for the lumbar vertebrae. In addition, the movements of a specific vertebra can be modified by the action of the surgeon as part of his operation, namely when he drills or breaks the bone structure, or cuts muscles and ligaments, which also support the vertebral structure.

In order to limit these movements during a lumbar surgery, when the access path permits such, the patient is lying on his stomach, taking care to leave the movements of the belly free below the level of the chest region. The patient is then immobilized in this position by mechanisms and accessories of the operating table. This particular prone position permits to significantly reduce the magnitude of the movements of the lumbar rachis.

However, the breathing and especially the external forces resulting from the operation generate mutually periodic and extemporaneous movements of the lumbar rachis of several millimeters, which the surgeon is then obliged to compensate for thanks to his dexterity and his visual acuity.

In the case of a robotic-assisted operation, it is extremely important to measure these motions for the robotic arm to automatically adjust to these movements, in order to maintain the improved robotic accuracy compared to that of the surgeon, while accompanying said movements with a speed of execution corresponding to the speed of the target.

To this end, in order to be in line with the pre-operative planning on 3D imaging, the movements of the anatomical target, namely the lumbar vertebra, should be measured and compensated for in real time in order to maintain the pinpoint accuracy of the device for assisting in location.

At present, the solution of the marker screwed into the backbone is carried out, namely during navigation. An algorithm then calculates the compensations in the location marker in the image, that is displayed and which are transmitted in real time to the robotic arm. However, this solution still has the disadvantage of being invasive. In addition, the optical recognition of the marker risks to be masked by the practitioner, which pass onto said calculation, generates differences in movement of the robotic arm relative to the anatomical movements thus captured.

Such a solution is described in part in US 2006/142657, which relates to a system comprising a first robotic arm and a second passive arm. Said first arm carries an instrument, namely a surgical instrument, while the second arm is made integral at its distal end with a marker anchored in the bone of the targeted anatomical area. Thus, the movement of the bone induces the movement of the marker that is captured by the passive arm, and then passed onto the robotic arm.

However, without imaging, this solution is limited to the operation of the bone itself and does not permit to compensate for movements of other tissues. In short, the mechanical anchoring in the bone permits to follow the movements of the area.

A non-invasive solution is devised through WO 2007/002926, which describes a robotic system for irradiating tissues for treating cancer. In particular, a radiation emitting source, "LINAC", is carried by a first robotic arm. A second arm serves only as a support for an ultrasonic probe positioned at the level of anatomical area to be treated and recording images of said area. These images are used for calculating the internal movements of the anatomical area.

However, the position in space of the probe is determined by a separate and additional optical system, which still causes the aforementioned problems.

This document also provides for using markers placed at the level of the anatomical area, directly on the skin. The detection of the movements of these markers permits to determine the external movements of the anatomical area.

In addition, a treatment based on a mathematical modeling is necessary to obtain the relative coordinates for correcting the trajectory of the LINAC, relative to the actually measured internal and external movements of the anatomical area. This calculation takes a significant processing time, making difficult its application in the context of an operation on an anatomical area such as the rachis, and always generates degrees of errors.

Another solution is described in DE 10 2008 022924. An imaging system carried by a robotic arm, referred to as "C-arm", is capable of performing a series of shots that, upon processing, will permit to display the movement of the targeted anatomical area.

However, the C-arm arm serves only as a support for and for positioning said imaging system, depending on the desired orientation of the shots to be taken. This arm is in no way made to follow said anatomical area in accordance with its movements. In brief, once it has been positioned, the arm remains static or its position is changed, without taking into consideration the movements of the target.

Furthermore, the monitoring of the movement of the area is achieved by markers in the form of pellets, glued to the outer portion of the anatomical area. Again, a separate optical or electromagnetic system permits to capture the movements of said markers and to deduce from same the external movements of said anatomical area. This deduction is performed by a mathematical processing in order to guide another robot, which carries an instrument, namely a surgical instrument.

Another related exemplary solution is mentioned in US 2008/033410, which describes a single robotic arm and a fixed support, initially set, without any movement being possible according to the movements being detected. Indeed, said support comprises tubes connected at their ends by collet fixtures, which keep them integral with respect to each other. In order to adjust their relative positions, it is then necessary to loosen said fixtures, change the orientation, then re-tighten the fixtures.

In addition, once again, this system uses a display by means of a not very accurate additional optical system.

SUMMARY OF THE INVENTION

The aim of the invention is to cope with the drawbacks of the state of the art by providing a device for positioning a surgical instrument relative to the body of a patient using at least a first robotic arm supporting at least one surgical instrument and a second tracker arm, which is also a robotic arm. This second robotic arm is aimed at detecting in real time and accurately the movements of said body and to communicate them to said first arm, so that it compensates its position accordingly. In particular, said second arm permits to detect the internal and external movements of the anatomic area to be treated.

On the one hand, the detection of internal movements is performed by suitable sensors, in particular by means of an ultrasonic probe positioned into contact with the skin of the patient, in front of the targeted anatomical area. From the internal movements so captured in real time, it is possible to pass the internal displacement to said first robotic arm, in order to compensate its trajectory.

In this respect, it should be noted that the positioning of the first robotic arm occurs in an initialization phase by means of a realignment of an image of the area acquired per-operatively with respect to a previously acquired imaging. Therefore, it is possible to modify this realignment, according to the internal movements detected by the sensors carried by the second arm.

On the other hand, the second arm moves under the action of movements of the anatomical area, since it is connected thereto, preferably by contact. These external movements of the area, induced to said second arm, can then be passed to said first arm. In brief, the second arm moves, since it is against the area and, since it is a robotic arm, it is possible to automatically know these movements with an extreme accuracy, in order to transmit them to said first arm.

Yet on the other hand, since said second arm is a robotic arm, its position is perfectly known. Since it carries the sensors, their position is, in turn, also known exactly. Thus, it is possible to omit an additional, namely optical, system for detecting the position of the sensors, which are directly integral with the end of said second arm.

To this end, the device according to the invention comprises:

a first robotic arm provided at one end with means for making it integral with at least one surgical instrument, so as to hold, move, position and guide said surgical instrument;

means for anatomically realigning said first arm relative to said body, said realignment being carried out by realigning an image of an area of the anatomy of said patient acquired per-operatively with respect to a previously acquired imaging;

sensors for detecting in real time the internal movements of said anatomical area, and means for compensating for the movements of said first arm according to said detected movement;

wherein it comprises:

at least one second robotic arm provided at one end with said sensors for detecting said internal movements of the anatomical area, said detection sensors being positioned at said contact with said anatomic area;

means for controlling the positioning of said first arm, on the one hand, relative to said internal movements detected and, on the other hand, relative to the external movements induced to said second arm.

Thus, the invention implements a robotic solution for assisting the guiding of surgical instruments, anatomical realignments and planning of the operating procedures for open, minimally invasive and percutaneous surgery, providing a measurement in real time of the movements of the area targeted by the operation, namely a lumbar vertebra, and compensating accurately said movements measured internally and externally, in order to position the robotic surgeon arm accordingly, while correcting its robotic trajectories and maintaining the accuracy of the guiding and the correct positioning of the instruments.

Furthermore, it should be noted that said second arm can then consist of means for referencing the positions in space of said detection sensors and that the means for controlling the positioning of said arm comprise means for taking into consideration the referencing of said positions.

In addition, said means for realigning can comprise means for acquiring by ultrasonic percutaneous recording or by marking the internal structure of said anatomical area by fluoroscopy.

Advantageously, said device can comprise means for measuring the forces of at least one of said arms during the contact with said anatomical area.

Preferably, said detecting means can comprise ultrasonic sensors for detecting said movements in real time through percutaneous measuring, namely by means of ultrasonic sensors.

In particular, the detection means can comprise at least one marker made integral with said anatomical area, in order to measure its movements in the space.

Finally, said marker can be a marker emitting an optical, ultrasound, electromagnetic, and/or mechanical signal, while the detection means can comprise the receiving of said signal by said reciprocally optical, ultrasound, electromagnetic and/or mechanical sensor. Therefore, the measurement of the movements is performed through the emitting of said signal by said marker, then this signal is received by said sensors.

BRIEF DESCRIPTION OF THE DRAWINGS

Further features and advantages of the invention will become clear from the following detailed description of non-restrictive embodiments of the invention.

The single FIGURE is a schematic view, representing the robotic device for an operation on a patient lying on an operating table in prone position.

DETAILED DESCRIPTION OF THE DRAWINGS

The present invention relates to the positioning of a robotic-assisted surgical tool relative to the body 1 of a patient and the correcting of such a positioning relative to the movements of said body 1.

The invention will be described by way of an example with reference to an anatomical area of said body 1, namely the rachis and more particularly the operation on a lumbar vertebra.

Thus, the invention relates to a device 2 for implementing in order to ensure an accurate positioning of at least one surgical instrument relative to the body 1 of a patient, in particular a determined anatomical area.

First of all, when implementing the device according to the invention, at least one surgical instrument is made integral with the end 30 of at least one first robotic arm 3, in order to maintain, move, position and guide said surgical instrument. Several arms can each support one or more instruments.

In particular, said first robotic arm 3 comprises several motorized and mutually articulated sections, so as to move in space. Said first robotic arm 3 has a fixed end 31, serving as a base and defining the three-dimensional location marker within which it evolves. The opposite distal end 30 has suitable means adapted for receiving removably fixed one or several surgical instruments. This distal end 30 can also comprise means for receiving sensors or measuring devices.

Thus, the first robotic arm 3 replaces or guides the practitioner's hand and holds the surgical tools.

Advantageously, said first arm 3 is positioned through anatomical realignment relative to said body 1. The latter occurs through realigning an image of an area of the anatomy of said patient per-operatively acquired relative to a previously acquired imaging.

In this respect, several realignment techniques can be used. They consist in collecting at the time of or during the operation images of the anatomical area of the patient, in order to accurately locate them in space and the marking of the surgical instruments carried by the first arm 3. To this end, the acquired images are compared and matched with previously acquired images, in pre-operative mode. Based on these pre-operative images, the positioning and the movement of the first robotic arm 3 is configured in order to perform the surgical procedures occurring during the operation.

It should be noted that the realignment can be performed on two- or three-dimensional images, by means of computer software.

An exemplary anatomical realignment methodology is described in detail in FR 2 917 598 and permits to capture within a three-dimensional space an anatomical surface of an area of interest of a patient's body. Subsequently, the shape measured per-operatively by the robot will be realigned on the image of a scanner previously taken pre-operatively, namely by means of a scanner of the Magnetic Resonance Imaging ("MRI") type. The surface recording operation is performed either by a mechanical probe carried by the robotic arm, entering into contact with said anatomical area, in order to record the positions of the probed points in the three-dimensional location marker of the robot, or by a contactless laser rangefinder carried by the robotic arm, and which scans the area of interest, in order to record the positions of the reflected points in a three-dimensional location marker of the robot.

This point recording method is superficial in both cases. In brief, it is applied to the outer surface of the patient's skin or of a previously prepared, namely dissected organ.

Starting from this methodology, it is possible to adapt the robotic arm for carrying an ultrasonic probe at its distal end.

In brief, the acquisition per-operatively or in real time is performed through ultrasonic percutaneous recording.

It is then possible to perform paths into contact with the patient's skin and to acquire percutaneously a cloud of points in the three-dimensional location marker of said robotic arm, so as to obtain for example the outer shape of a bone.

In brief, the ultrasound probe and its associated system for processing the so acquired data are used in the way of a rangefinder, in order to determine the position of the points where the ultrasounds will be reflected, because of a clean break of the composition of the biological components, namely the difference in bone-muscle density inducing a high reflection coefficient between both of them, while this ratio is low for a combination of layers of skin, muscle, fat and water. It is thus possible to measure percutaneously the position of a bone surface through a layer of muscle and the skin.

Depending on the type of operation and the targeted anatomical area, said probe can emit ultrasounds at frequencies of about 5 to 8 MHz (Megahertz).

Subsequently, the three-dimensional shape measured per-operatively by the robotic arm will be realigned to the form resulting from the three-dimensional image from the scanner previous made pre-operatively Namely, segmentation tools will previously permit to isolate the anatomical region of interest on the pre-operative image, namely a bone, such as a vertebra in the present example. This thus provides an initial realignment serving as a reference for tracking the movements.

In this very case, said robotic arm will carry several ultrasound transceivers placed into contact with the skin, in front of remarkable surfaces of the vertebra, accessible from a prone position of the patient (posterior approach). The discriminant shapes of the blades, the spine and the transverse apophyses of said vertebra are capable of providing enough information to reconstruct in real time the three-dimensional image of the vertebra. Then, by matching the three-dimensional image or remarkable points, the images of the vertebra acquired per-operatively are superposed with pre-operative images, so as to locate it in the location marker of said robotic arm.

Thus, such a realignment is non-invasive. In brief, the system is capable of identifying the internal anatomical structure, for example a lumbar vertebra, without previous dissection.

Another realignment solution can use a two- or three-dimensional fluoroscopy method. In brief, the per-operative acquisition occurs by identifying the internal structure of said anatomical area by fluoroscopy. However, the use of ultrasounds has the advantage of omitting the harmful radiation of fluoroscopy.

It should be noted that fluoroscopy can be used complementarily to ultrasound, for example, in order to obtain a reference anatomical realignment, or at given times during the operation, thus limiting the radiation. These reference and complementary realignments will namely permit the continuation of other anatomical realignments made, in order to control them, but also to assist in bringing the various robotic arms together within the same three-dimensional location marker, thanks to a tracking marker carried by one of the robotic arms.

Therefore, the fluoroscopic-radiation emitting system can be provided on the operating table, on which the patient is placed for the operation, while the tracking marker is carried by the robotic arm.

According to an essential feature of the present invention, the movements of said anatomical area are then captured and the displacements of said first arm are compensated for based on the captured movements.

In brief, the invention provides for real-time measurement of the amplitude, the direction of the movements of the patient's body, in particular of the anatomical area within the location marker of said first robotic arm 3, in order to change its trajectories accordingly, even to anticipate said movements and to correct the paths in advance.

Advantageously, the invention consists in positioning sensors detecting said movements of the anatomical area into contact with said anatomical area, said sensors being integral with the end of at least one second arm 4. According to the embodiment, such a second arm 4 can be motorized in a robotic version, i.e., it is provided with several sections motorized between them, like the first robotic arm 3.

In brief, the second robotic arm is motorized at the level of its joints, so as to move and be positioned in space according to the instructions previously transmitted to said motorizations.

Conversely, the displacement in space of this second arm 4 can be directly known. In brief, when the distal end of the second arm 4, held into contact or made integral with the anatomical area, moves, then this movement is passed to the motorized joints of the various sections forming said second arm 4. The movements of the joints thus permit to exactly know the displacement of each section and the movement of said second arm 4.

In addition, since the second arm 4 is in the same or a different location marker, but the transposition of which is known relative to the location marker of the first arm 3, the invention provides to directly pass the movement of said second arm 4 in order to change the displacements of said first arm 3.

In brief, the physical displacements of the second arm 4 are transmitted and applied to the first arm 3 already in motion.

Thus, the invention captures the internal movements of the anatomical area and its external movements, which induce the displacements of the second robotic arm 4. These internal, external movements and the displacements of the second arm 4 are applied in order to change the trajectory of the first arms 3.

More particularly, the invention consists in detecting said internal and external movements and the displacements by means of said sensors and said second arm and in controlling the position of said first arm 3.

Moreover, the control occurs through dedicated means, formed at least in part by means for controlling the displacements of said first arm 3. In addition, these control means permit to receive the measurements of the internal and external displacements of the anatomical area as well as of the second robot arm 4, in order to combine these measurements and to transcribe them, in order to apply the results to the path of said first arm 3.

Thus, the invention involves one or more secondary arms 4, in order to accurately measure the movements of the patient's body 1, in order to correct the positioning of said first arm 3 and to maintain the guiding of the operation foreseen in the pre-operative planning. In brief, said second arm 4, due to its accuracy, provides the first arm 3 with an accurate and repeatable compensation for said movements.

To this end, said first 3 and second 4 arms operate separately or independently: one 3 of them positions the surgical instrument, while the other one 4 provides the information for maintaining a proper positioning.

In the exemplary application to a vertebra, the second arm 4 follows the movements of the latter and transmits these changes to said first arm 3. As mentioned above, these changes can be internal and external, without inducing any displacement of said second arm 4, but also and especially when these movements cause its displacement.

According to a specific feature, said first robotic arm 3 and the second robotic arm 4 can include one and the same three-dimensional location marker in which they evolve. In other words, said second robotic arm 4 is formed in a similar way as the first arm 3 and has a base 40 located in one and the same location marker as the base of said first robotic arm 3.

In another embodiment, said second arm 4 can evolve within a different location marker, but defined relative to the location marker of said first arm 3, permitting through a calculation step, a transposition of the coordinates from one to another. The second arm 4 thus permits to change its location marker and the location marker for measuring the internal and external movements during the operation, while calculating its connection to the location marker of the first arm 3.

In addition, according to a preferred embodiment, the invention consists in measuring the forces of at least one of said arms 3, 4 during the contact with said anatomical area. In particular, each of the first 3 and second 4 arm is provided with at least one force sensor at its respective distal end 30 and 41.

This measurement of the force permits to check and configure the force applied to the surgical instruments, as well as to the various sensors and measuring devices. In addition, it permits to provide a cooperative mode in which the practitioner can manipulate the end 30 of said first arm 3 so as to be guided during the operation.

In the case of the second arm 4, the force sensor permits to maintain a suitable pressure, ensuring a good contact of the sensors with the anatomical area, namely the skin.

In this respect, according to a first embodiment, the detection of the internal movements of the anatomical area can occur through percutaneous measurement by means of ultrasonic sensors. This technique is similar to the one previously evoked for the reference anatomical realignment.

In this very case and in the described exemplary embodiment, said robotic arm, in particular the second arm 4, will carry several ultrasonic transceivers placed into contact with the skin, in front of remarkable surfaces of the vertebra, accessible from a prone position of the patient (posterior approach). The discriminant shapes of the blades, the spine and the transverse apophyses of said vertebra are capable of providing enough information to reconstruct in real time the three-dimensional movement of the vertebra.

It is however possible to use local realignments of the remarkable points with the images of the vertebra acquired pre-operatively, in order to optimize the search for the exact position of the vertebra in motion. Then, by calculating the change in coordinates, the reference realignment is updated, in order to use it in the working location marker of the robotic arms 3, 4.

Furthermore, the ultrasonic transceivers are placed into contact with the skin by the second robotic arm 4 in known, permitting to follow the external positions movements of the anatomical area. In brief, the coordinates in space of the contact point or surface of the sensors is known, since said sensors are carried by the second robotic arm 4.

In this context, said second arm 4 consists in means for referencing the positions in space of said detection sensors and the means for controlling the positioning of said arm 3 comprise means for taking into consideration the referencing of said positions.

This solution still has the advantage of being non-invasive. In addition, the system is capable of detecting the movements of the internal structure, e.g., a lumbar vertebra, without previous dissection.

According to another embodiment, the detection of the internal movements occurs through measuring the displacements in space of at least one marker made integral with said anatomical area. In particular, in the example of a vertebra, said marker is screwed invasively into the spine or other preferred bone areas, per-operatively.

Thus, the marker and the vertebra become integral with one another. Moreover, the implantation position of said marker relative to the vertebra can be accurately determined, knowing that the position of the vertebra in the location marker of the arms 3, 4 can already be known previously through the reference anatomical realignment; this through acquisition of images, namely by fluoroscopy or ultrasounds.

Once the reference position has been determined, the position of the location marker in the reference arms 3, 4 is measured, then updated periodically or continuously.

In this respect, according to various embodiments, the measurement of the displacements occurs through emission by said marker of an optical, ultrasound, electromagnetic, and/or mechanical signal, then by receiving said signal by said reciprocally optical, ultrasound, electromagnetic and/or mechanical sensors.

More particularly, said marker can be connected directly to said sensors in the form of a mechanical connection with the distal end 41 of the second arm 4. Therefore, in the latter case, said mechanical connection can be designed hinged, namely in the form of a geometric lattice. Such a lattice has the advantage of increasing the amplitude of the movements being measured, in order to obtain greater accuracy for correcting the position of the first robotic arm 3.

It should be noted that the corrections of this position can be made relative to the origin of the axis of the location marker of said first arm 3, relative to the initial position, or relative to the current position of its distal end 30.

Furthermore, said force sensor may be adjusted so as to optimize the measurement of the movements perceived by this mechanical connection.

Thus, the measure of the internal and external movements recorded by the second arm 4 is provided to said first arm 3, which uses it to correctly reposition the surgical instrument it supports on the anatomical target, depending on the previously planned trajectory. In addition, this measure permits to correct in real time and to automatically update the anatomical realignment being performed, even during the displacement of the surgical instrument.

According to an additional feature, the detected anatomical movements can be anticipated, in particular by simulations of periodic movements of the anatomical area. In the example of the lumbar rachis, respiratory movements can be known, namely their period and amplitude, in order to be taken into consideration in changing the trajectory.

As mentioned above, the invention relates to a robotic device 2 for positioning a surgical instrument relative to the body 1 of a patient.

Such a device 2 is similar to a robotic platform 5 and thus comprises a first robotic arm 3 provided at one end with connecting means 30 making it integral with at least one surgical instrument; means for anatomically realigning said first arm 3 relative to said body 1, said realignment occurring through realignment of an image of an area of the anatomy of said patient acquired per-operatively relative to a previously acquired imaging; means for detecting the internal movements of said anatomical area and means for compensating in real time for the displacements of said first arm 3 depending on said movements being detected.

Advantageously, it is characterized in that it comprises at least one second robotic arm 4 provided at one end with said sensors for detecting said internal movements of the anatomical area; means for controlling the positioning of said first arm 3, on the one hand, relative to said internal movements being sensed and, on the other hand, relative to the external movements induced to said second arm 4.

Thus, the present invention permits to ensure the robotic accuracy during the positioning of a surgical instrument at the level of an anatomical area, while adapting to the movements of the body of the patient.

Moreover, the use of a second robotic arm permits to obtain data regarding the external movements, without involving additional or complementary systems for detecting the position of the sensors.

What is claimed is:

1. An automated robotic surgical assistance device comprising:
   an ultrasound transceiver disposed at a distal end of a robotic arm, the ultrasound transceiver configured, without previous dissection, to:
   capture ultrasonic data while maintaining contact with skin of a patient n line with at least one vertebra of the patient; and
   a computing circuitry in operative communication with the robotic arm, the computing circuitry configured to:
   receive ultrasonic data from the ultrasound transceiver;
   generate a real-time three-dimensional image of the at least one vertebra; and
   register the real-time three-dimensional image to a pre-operative image of the at least one vertebra.

2. The automated robotic surgical assistance device of claim 1, wherein the at least one vertebra is a lumbar vertebra.

3. The automated robotic surgical assistance device of claim 1, wherein the at least one registration of the real-time three-dimensional image to the pre-operative image of the at least one vertebra includes a reference for tracking movement of the at least one vertebra per-operatively.

4. The automated robotic surgical assistance device of claim 1, wherein the ultrasound transceiver is configured to emit ultrasound at frequencies of about five to eight MHz.

5. The automated robotic surgical assistance device of claim 1, wherein the ultrasonic data includes a cloud of three-dimensional location points along an outer portion of the at least one vertebra.

6. The automated robotic surgical assistance device of claim 1, wherein the ultrasound transceiver is configured to maintain contact via automated movement of the robotic arm in response to the detected movement of the skin.

7. The automated robotic surgical assistance device of claim 1, wherein the ultrasound transceiver comprises at least one marker attached to the skin, the least one marker used to provide a position of the ultrasound transceiver.

8. The automated robotic surgical assistance device of claim 1, wherein the automated robotic surgical assistance device further comprises a force measuring element coupled to the robotic arm and configured to detect force exerted by the skin on the robotic arm.

9. At least one non-transitory machine-readable medium including instructions for using an automated robotic surgical assistance system, which when executed by a machine, cause the machine to:
   capture, via an ultrasound transceiver disposed at a distal end of a robotic arm, ultrasonic data without previous dissection while maintaining contact with skin of a patient in line with at least one vertebra of the patient;
   generate a real-time three-dimensional image of the at least one vertebra; and
   register the real-time three-dimensional image to a pre-operative image of the at least one vertebra.

10. The at least one machine-readable medium of claim 9, wherein the at least one vertebra is a lumbar vertebra.

11. The at least one machine-readable medium of claim 9, wherein the at least one registration of the real-time three-dimensional image to the pre-operative image of the at least one vertebra includes a reference for tracking movement of the at least one vertebra per-operatively.

12. The at least one machine-readable medium of claim 9, wherein the ultrasound transceiver is configured to emit ultrasound at frequencies of about five to eight MHz.

13. The at least one machine-readable medium of claim 9, wherein the ultrasonic data includes a cloud of three-dimensional location points along an outer portion of the at least one vertebra.

14. The at least one machine-readable medium of claim 9, further comprising instructions that cause the machine to control automated movement of the robotic arm to maintain the contact of the ultrasound transceiver with the skin of the patient in line with at least one vertebra of the patient, in response to the detected movement of the skin.

15. The at least one machine-readable medium of claim 9, further comprising instructions that cause the machine to provide a position of the ultrasound transceiver using at least one marker attached to the skin.

16. The at least one machine-readable medium of claim 9, further comprising instructions that cause the machine to detect force exerted by the skin on the robotic arm using a force measuring element coupled to the robotic arm.

17. A method for using an automated robotic surgical assistance system, the method comprising:
   capturing; via an ultrasound transceiver disposed at a distal end of a robotic arm, ultrasonic data without previous dissection while maintaining contact with skin of a patient in line with at least one vertebra of the patient;
   generating a real-time three-dimensional image of the at least one vertebra; and
   registering the real-time three-dimensional image to a pre-operative image of the at least one vertebra.

18. The method of claim 17, wherein the at least one vertebra is a lumbar vertebra.

19. The method of claim 17, wherein the at least one registration of the real-time three-dimensional image to the pre-operative image of the at least one vertebra includes a reference for tracking movement of the at least one vertebra per-operatively.

20. The method of claim 17, wherein the ultrasound transceiver is configured to emit ultrasound at frequencies of about five to eight MHz.

* * * * *

UNITED STATES PATENT AND TRADEMARK OFFICE
CERTIFICATE OF CORRECTION

PATENT NO. : 10,667,876 B2  
APPLICATION NO. : 16/225693  
DATED : June 2, 2020  
INVENTOR(S) : Maillet et al.

Page 1 of 1

It is certified that error appears in the above-identified patent and that said Letters Patent is hereby corrected as shown below:

On page 3, in Column 1, under "Other Publications", Line 8, delete "datd" and insert --dated-- therefor On page 3, in Column 2, under "Other Publications", Line 38, delete "submtted" and insert --submitted-- therefor In Column 11, Line 29, in Claim 1, delete "n" and insert --in-- therefor In Column 12, Line 45, in Claim 17, delete "capturing;" and insert --capturing,-- therefor Signed and Sealed this  
Tenth Day of November, 2020

Andrei Iancu  
*Director of the United States Patent and Trademark Office*